United States Patent [19]

Soula et al.

[11] Patent Number: 4,629,801
[45] Date of Patent: Dec. 16, 1986

[54] PREPARATION OF HYDROGENOSILANES

[75] Inventors: Gerard Soula, Meyzieu; Jean-Luc Lepage, Sainte Foy Les Lyon, both of France

[73] Assignee: Rhone-Poulenc Specialites Chimiques, Courbevoie, France

[21] Appl. No.: 825,818

[22] Filed: Feb. 4, 1986

[30] Foreign Application Priority Data

Feb. 4, 1985 [FR] France ................................ 85 01486

[51] Int. Cl.$^4$ ................................................ C07F 7/08
[52] U.S. Cl. ..................................................... 556/466
[58] Field of Search ......................................... 556/466

[56] References Cited
PUBLICATIONS

Noll, "Chemistry and Technology of Silicones" Academic Press, N.Y. (1968), pp. 87–88.

Primary Examiner—Paul F. Shaver
Attorney, Agent, or Firm—Burns, Doane, Swecker & Mathis

[57] ABSTRACT

Hydrogenosilanes, notably the monosilanes, are conveniently prepared by reducing a halogenosilane with an alkali or alkaline earth metal hydride, typically in a solvent reaction medium, in the presence of a catalytically effective amount of a sequestering agent having the general formula:

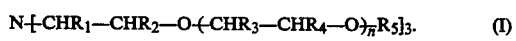

$$N\text{-}[CHR_1\text{---}CHR_2\text{---}O\text{-}(CHR_3\text{---}CHR_4\text{---}O)_n R_5]_3. \quad (I)$$

15 Claims, No Drawings

PREPARATION OF HYDROGENOSILANES

BACKGROUND OF THE INVENTION

1. Field of the Invention

The present invention relates to the preparation of hydrogenosilanes, and, more especially, to the preparation of monosilanes.

2. Description of the Prior Art

Processes for the production of monosilanes by reduction of silicon halides utilizing reducing agents such as lithium aluminum hydride, or lithium or sodium hydrides, are known to this art.

The reduction of silicon halides by LiAlH$_4$ is described, in particular, in the Kirk-Othmer *Encyclopedia of Chemical Technology*, Vol. 20, Third Edition, pages 887–911 (906) (1982). This reaction is carried out in a solvent medium, but in light of the very high cost thereof it is of little use industrially.

Reduction by sodium or lithium hydrides is specifically described in the aforecited reference for LiAlH$_4$; it requires operating at high temperatures in polar solvents or in a molten salt medium because of the slight solubilization of lithium hydride.

SUMMARY OF THE INVENTION

Accordingly, a major object of the present invention is the provision of an improved process for the reduction of the silane halides utilizing an alkali or alkaline earth metal hydride, in the presence of a particular catalyst, and which process is conspicuously devoid of those disadvantages and drawbacks to date characterizing the state of this art and even provides the following added advantages:

(i) the amount of the catalyst employed is very low;

(ii) the reduction may be carried out at about room temperature and thus it is possible, notably, to eliminate potential secondary reactions;

(iii) it permits carrying out the reaction in the presence of hydrides which ostensibly have very low efficiency, such as, for example, calcium hydride; and (iv) it makes it possible to use low boiling point industrial solvents.

Briefly, the process according to the present invention features the preparation of hydrogenosilanes by reduction of corresponding halogenosilanes with an alkali or alkaline earth metal hydride, typically in a solvent medium, and in the presence of a catalytically effective amount of a sequestering agent catalyst having the general formula:

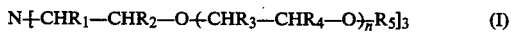  (I)

wherein n is an integer greater than or equal to 0 and less than or equal to 10 (0≦n≦10), R$_1$, R$_2$, R$_3$ and R$_4$, which may be identical or different, represent a hydrogen atom or an alkyl radical having from 1 to 4 carbon atoms and R$_5$ represents an alkyl or cycloalkyl radical having from 1 to 12 carbon atoms, a phenyl radical or a —C$_m$H$_{2m}$—φ or C$_m$H$_{2m+1}$—φ— radical, wherein m ranges from 1 to 12 (1≦m≦12) and φ is phenyl.

DETAILED DESCRIPTION OF THE INVENTION

More particularly according to the present invention, the subject process is advantageously represented by the following reaction sequence:

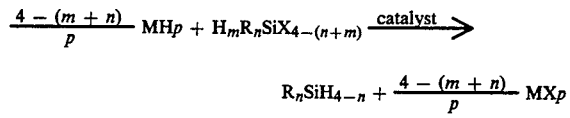

wherein the R radicals, which may be identical or different, represent an alkyl, aryl and/or alkoxy group; X represents a halogen, preferably chlorine, and M is an alkali or alkaline earth metal, preferably lithium, sodium, calcium or magnesium, n is an integer equal to 0, 1, 2 or 3, m is an integer equal to 0, 1, 2 or 3, m+n≦3 and p represents the valence of the alkali or alkaline earth metal.

The silane halides, or halogenosilanes, according to this invention are those of the formula R$_n$H$_m$SiX$_{4-(n+m)}$, wherein n is 0, 1, 2 or 3, and m is 1, 2 or 3 and R, when present, is selected from among alkyl and aryl radicals, and/or alkoxy radicals, and preferably is methyl, ethyl, propyl, isopropyl, methoxy, ethoxy, and/or phenyl, and X is a halogen, preferably a chloride. In a preferred embodiment of the invention, silicon tetrachloride, trichlorosilane, dichlorosilane, dimethyldichlorosilane, methylhydrogenodichlorosilane, diphenyldichlorosilane, phenyltrichlorosilane, methylphenyldichlorosilane, phenyltrichlorosilane, methylphenyldichlorosilane or diethyldichlorosilane, or mixtures thereof, are used.

The alkali or alkaline earth metal hydrides, MH$p$, employed according to the invention are preferably selected from among lithium hydride, sodium hydride, calcium hydride or magnesium hydride.

Consistent herewith, the catalyst is a sequestering agent having the general formula:

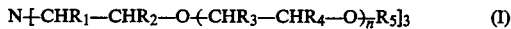  (I)

wherein n is an integer greater than or equal to 0 and less than or equal 10 (0≦n≦10), R$_1$, R$_2$, R$_3$ and R$_4$, which may be identical or different, each represents a hydrogen atom or an alkyl radical having from 1 to 4 carbon atoms and R$_5$ represents an alkyl or cycloalkyl radical having from 1 to 12 carbon atoms, a phenyl radical or a —C$_m$H$_{2m}$—φ or C$_m$H$_{2m+1}$—φ— radical, wherein m ranges from 1 to 12 (1≦m≦12) and φ is phenyl.

In another preferred embodiment of the invention, a sequestering agent of the formula (I) is used, wherein R$_1$, R$_2$, R$_3$ and R$_4$ each represents a hydrogen atom or a methyl radical, with R$_5$ and n being as above defined.

Among such preferred sequestering agents, it is even more particularly preferred to use those sequestering agents in which n is greater than or equal to 0 and less than or equal to 6 and in which R$_5$ is an alkyl radical having from 1 to 4 carbon atoms.

The following sequestering agents are noted as illustrative:

[1] tris-(3-oxabutyl)-amine of the formula: N—(CH$_2$—CH$_2$—O—CH$_3$)$_3$

[2] tris-(3,6-dioxaheptyl)-amine of the formula: N—(CH$_2$—CH$_2$—O—CH$_2$—CH$_2$—O—CH$_3$)$_3$

[3] tris-(3,6,9-trioxadecyl)-amine of the formula: N—(CH$_2$—CH$_2$—O—CH$_2$—CH$_2$—O—CH$_2$—CH$_2$—O—CH$_3$)$_3$

[4] tris-(3,6-dioxaoctyl)-amine of the formula: N—(CH$_2$—CH$_2$—O—CH$_2$—CH$_2$—O—C$_2$H$_5$)$_3$

[5] tris-(3,6,9-trioxaundecyl)-amine of the formula: N—(CH$_2$—CH$_2$—O—CH$_2$—CH$_2$—O—CH$_2$—CH$_2$—O—C$_2$H$_5$)$_3$

[6] tris-(3,6-dioxanonyl)-amine of the formula: N—(CH$_2$—CH$_2$—O—CH$_2$—CH$_2$—O—C$_3$H$_7$)$_3$

[7] tris-(3,6,9-trioxadodecyl)-amine of the formula: N—(CH$_2$—CH$_2$—O—CH$_2$—CH$_2$—O—CH$_2$—CH$_2$—O—C$_3$H$_7$)$_3$

[8] tris-(3,6-dioxadecyl)-amine of the formula: N—(CH$_2$—CH$_2$—O—CH$_2$—CH$_2$—O—C$_4$H$_9$)$_3$

[9] tris-(3,6,9-trioxatridecyl)-amine of the formula: N—(CH$_2$—CH$_2$—O—CH$_2$—CH$_2$—O—CH$_2$—CH$_2$—O—C$_4$H$_9$)$_3$

[10] tris-(3,6,9,12-tetraoxatridecyl)-amine of the formula: N—(CH$_2$—CH$_2$—O—(CH$_2$—CH$_2$—O)$_3$—CH$_3$)$_3$ and

[11] tris-(3,6,9,12,15,18-hexaoxanonadecyl)-amine of the formula: N—(CH$_2$—CH$_2$—O—(CH$_2$—CH$_2$—O)$_5$—CH$_3$)$_3$ The following sequestering agents are also representative:

[12] tris-(3,6-dioxa-4-methylheptyl)-amine of the formula:

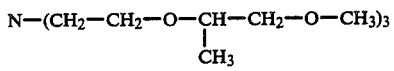

and

[13] tris-(3,6-dioxa-2,4-dimethylheptyl)-amine of the formula:

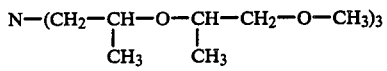

The amine sequestering agents utilized in the process according to the invention are per se known to the prior art. Thus, French Pat. No. 1,302,365 describes the preparation of the tertiary amines

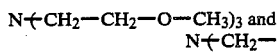

as by-products from the synthesis of the corresponding primary and secondary amines, such primary and secondary amines being valuable as intermediates in the synthesis of various pharmaceuticals, as corrosion inhibitors, as intermediates in the synthesis of agricultural chemicals, and as emulsifiers. It will also be appreciated, though, that the prior art, including the aforenoted French Pat. No. 1,302,365, is conspicuously devoid of any suggestion that the topic amines could be utilized in any reaction within the ambit of this invention.

In another embodiment of the invention, the sequestering agent may be grafted onto a cross-linked organic polymer and, thus, the present invention also features a process for the preparation of hydrogenosilanes by reduction of a silane halide utilizing an alkaline hydride, in a solvent reaction medium, in the presence of a catalyst, characterized in that the catalyst is a graft sequestering agent consisting of a cross-linked organic polymer support and a plurality of functional groups grafted onto said support as depicted in the general formula below:

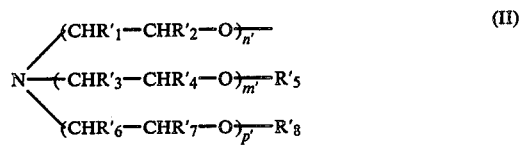

wherein R'$_1$, R'$_2$, R'$_3$, R'$_4$, R'$_6$ and R'$_7$, which may be identical or different, are each a hydrogen atom or an alkyl radical having from 1 to 4 carbon atoms, R'$_5$ and R'$_8$, which also may be identical or different, are each a hydrogen atom, an alkyl or cycloalkyl radical having from 1 to 12 carbon atoms, a phenyl radical, a —C$_q$H$_{2q'}$—$\phi$ or C$_{q'}$H$_{2q'+1}$—$\phi$— radical, with q' being greater than or equal to 1 and less than or equal to 12, and wherein n', m' and p', which also may be identical or different, are greater than or equal to 1 and less than or equal to 10.

In another embodiment of the invention, a supported sequestering agent is used which comprises a cross-linked organic polymeric support having a plurality of functional groups grafted thereon and which has the aforesaid formula (II), wherein R'$_1$, R'$_2$, R'$_3$, R'$_4$, R'$_6$ and R'$_7$, which may be identical or different, are each a hydrogen atom or a methyl radical and R'$_5$ and R'$_8$, which may be identical or different, are each a hydrogen atom or an alkyl radical having from 1 to 4 carbon atoms. In yet another preferred embodiment of the invention, n', m' and p', which may be identical or different, are greater than or equal to 1 and less than or equal to 6.

As examples of the functional groups which are grafted onto the polymeric substrate, the following are representative:

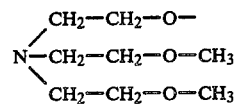

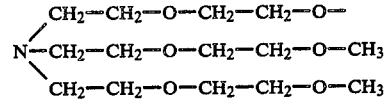

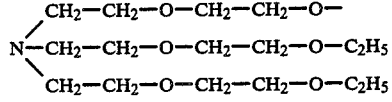

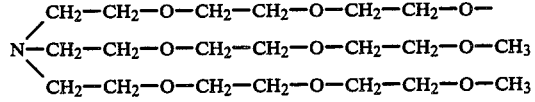

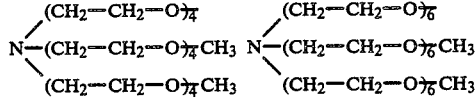

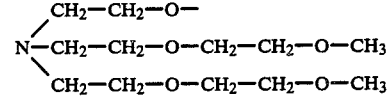

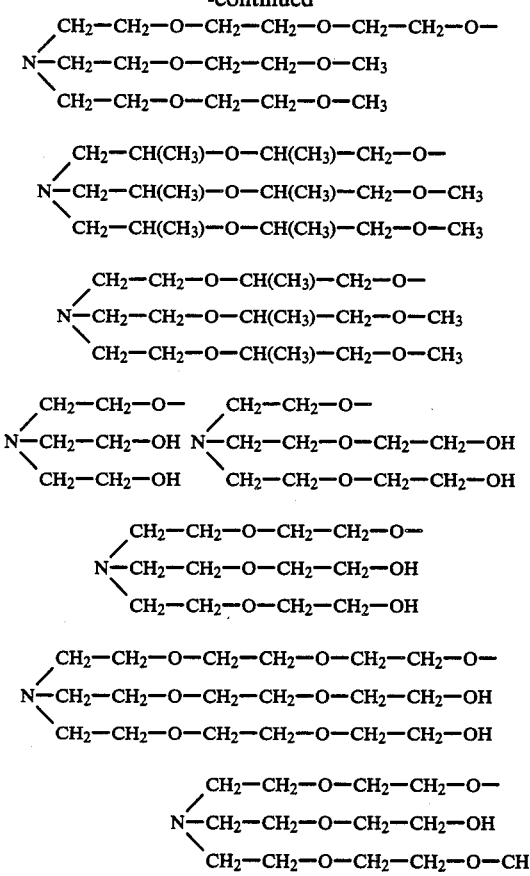

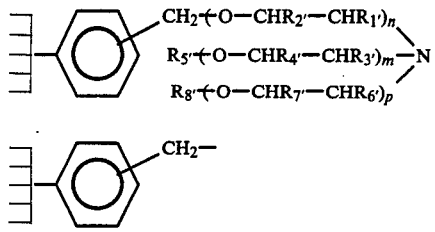

The support for the above functional groups can be derived from any crosslinked organic polymer containing moieties which can be substituted by the functional groups of the formula (II).

Examples of organic polymers suitable as supports in the process of the present invention are polymers derived from vinyl aromatic compounds such as styrene and methylstyrene, and copolymers of vinyl aromatic compounds with $C_4$-$C_6$ conjugated dienes, such as styrene/butadiene and styrene/isoprene copolymers.

Particularly preferred for use in the invention is polystyrene and in a preferred embodiment divinylbenzene is employed therewith as the crosslinking agent. The degree of crosslinking is an important factor inasmuch as it is necessary that the functional groups of the formula (II) grafted onto the polystyrene support be active. Accordingly, the molecules of the solvent in which the supported sequestering agent is to be used in the application of the present invention must penetrate the interstices of the polymer. To achieve this end, the degree of crosslinking must not be so high that it prevents the solvent and the reactants from penetrating and, accordingly, preferred polystyrenes are those with a degree of divinylbenzene crosslinking less than about 10%. Even more preferably, the degree of crosslinking is less than about 5%.

Typical groups which can be substituted with the aforementioned functional groups are the chlorine or the bromine of chloromethyl or bromomethyl groups, i.e., —$CH_2Cl$ or —$CH_2Br$, on the benzene nucleus of the polystyrene. With respect to such substituted benzene moieties, it is particularly preferred for the percentage of benzene nuclei of the polystyrene which carry a functional group to be more than 5% and, even more preferably, more than 10%.

The preferred supported sequestering agents can be represented by the following formula:

and which are derived from chloromethylated or bromomethylated polystyrene cross-linked by divinylbenzene of the formula:

where X represents Cl or Br.

The process according to the invention is typically and preferably carried out in the presence of a solvent(s), and advantageously the sequestering agent itself is used as the solvent. The solvent must satisfy a number of conditions: it must solubilize the halogenosilane starting material; it must be chemically inert with respect to the silanes introduced or formed, as well as with respect to the alkali or alkaline earth metal hydride. The minimum amount of solvent used is preferably such that the alkali or alkaline earth metal hydride used is in suspension in the reaction medium.

Preferably a solvent is used such as, for example, chlorobenzene, ortho-dichlorobenzene, benzene, toluene, cyclohexane, heptane, dichloroethane, methylene chloride, tetrahydrofuran, dioxane and dimethoxyethane.

The process of the invention is advantageously carried out at a temperature of from —30° C. to the boiling temperature of the reaction medium, and preferably from room temperature to the boiling temperature of the reaction mixture. In the latter case, the product hydrogenosilane may be separated at the rate at which it is formed. It is possible to carry out the reaction at about room temperature, i.e., from 0° to 50° C.; this circumscribes one of the primary advantages of the process of the invention.

It is preferred to operate at atmospheric pressure. It will be appreciated, however, that pressures higher or lower than atmospheric are also within the ambit of the invention.

According to this invention, the molar ratio between the sequestering agent and the alkali or alkaline earth metal hydride advantageously ranges from 5 to 0.0001 and preferably from 0.5 to 0.001.

The molar proportion between the hydride and the silane halide is generally close to stoichiometry. A slight excess of the hydride may, however, be preferable to completely reduce the silane halide. This excess is preferably from 10 to 300 molar %.

The reduction reaction is preferably carried out by slowly introducing the silane halide into the reaction medium and it may be further advantageous to cool the reaction medium in order to avoid an excessive increase in temperature which would favor the secondary reactions of formation of byproducts.

The hydrogenosilanes obtained via the subject reduction reaction may be separated at the rate of their formation.

The grafted sequestering agents used according to the invention make it possible to carry out the subject reaction, preferably continuously, in a column, while the ungrafted sequestering agents permit preferably discontinuous operations.

The sequestering agents having the formula (I) which are employed in the process according to the invention may be prepared as described in the French application, published under No. 2,450,120.

The present invention thus makes it possible to carry out the reduction of halogenosilanes at room temperature and with an exceptional productivity, while at the same time using but small amounts of the catalyst.

In order to further illustrate the present invention and the advantages thereof, the following specific examples are given, it being understood that same are intended only as illustrative and in nowise limitative.

EXAMPLE 1

Synthesis of $(C_6H_5)_2SiH_2$ by reduction of $(C_6H_5)_2SiCl_2$ with LiH

Into a 1 liter flask equipped with a blade agitator and surmounted by a reflux condenser and a dropping funnel, the following materials were introduced, after flushing with argon:

(i) 69.24 g tris(3,6-dioxaheptyl)amine (hereafter TDA-1), or 0.214 mole, (ii) 31.5 g LiH, or 3.96 moles.

Under agitation, 501 g $(C_6H_5)_2SiCl_2$, or 1.97 mole, were added thereto drop-by-drop. Duration of the addition: 6 hours.

The reaction medium was heated to 50° C. at the onset of the pouring, in order to initiate the reduction of the diphenyldichlorosilane. Following the initiation of the reaction, the significant exothermy of the reaction made it possible to maintain the temperature of the reaction medium at approximately 120° C. Slight heating was necessary upon completion of the pouring to maintain this temperature. The reaction medium was heated to 130°–150° C. for one hour after the addition of the $(C_6H_5)_2SiCl_2$.

A gas phase chromatographic analysis upon completion of the reaction evidenced the following composition (by weight):

$(C_6H_5)_2SiH_2$: 48%
$(C_6H_5)_2SiHCl$: 2%
$(C_6H_5)_2SiCl_2$: 50%

This corresponded to a proportion of conversion of $(C_6H_5)_2SiCl_2$ of 58% and a selectivity in $(C_6H_5)_2SiH_2$ of 97%.

Following the elimination of the solid phase by filtration (LiCl formed and the unreacted LiH), the product diphenylsilane was separated from the other phenylsilanes by fractionating distillation in vacuum: $(C_6H_5)_2SiH_2$ distilled at 78° C. under 0.5 mmg Hg and $(C_6H_5)_2SiCl_2$ at 110° C. under the same vacuum.

A diphenylsilane was thus obtained, having a purity higher than 98.7%.

EXAMPLE 2

Synthesis of $C_6H_5SiH_3$ by reduction of $C_6H_5SiCl_3$ with LiH

In this example, reductions of $C_6H_5SiCl_3$ with LiH were carried out in the presence of TDA-1 and in a chlorobenzene reaction medium, by varying the $LiH/C_6H_5SiCl_3$ ratio.

Apparatus used: 50 ml flask with magnetic agitation surmounted with a reflux condenser and a dropping funnel.

Phenyltrichlorosilane was introduced by means of the dropping funnel into the flask containing the TDA-1, the solvent and the lithium hydride.

The reaction commenced at the onset of the addition, at room temperature; the significant exothermy made it necessary to cool the reactor in order to maintain the temperature below 80° C.

Upon completion of the pouring addition, the duration of which was on the order of 15 min, the reaction medium was heated to 120° C.

In the following table, the different experiments carried out are reported, together with the results obtained, the composition of the reaction medium upon completion of the addition of $C_6H_5SiCl_3$ and after heating, the corresponding proportion of the conversion of phenyltrichlorosilane and the selectivity in respect of $C_6H_5SiH_3$:

TABLE

| | No. of experiment | | | | |
|---|---|---|---|---|---|
| | 1 | 2 | 3 | 4 | 5 |
| CHARGE | | | | | |
| LiH | 1.064 g ($13.4 \cdot 10^{-2}$ moles) | 1.456 g ($18.3 \cdot 10^{-2}$ moles) | 1.733 g ($21.8 \cdot 10^{-2}$ moles) | 3.121 g ($26.7 \cdot 10^{-2}$ moles) | 1.564 g ($19.7 \cdot 10^{-2}$ moles) |
| TDA-1 | 1.811 g ($0.56 \cdot 10^{-2}$ moles) | 1.908 g ($0.59 \cdot 10^{-2}$ moles) | 2.005 g ($0.62 \cdot 10^{-2}$ moles) | 1.973 g ($0.61 \cdot 10^{-2}$ moles) | |
| $C_6H_5Cl$ | 13.68 g ($12.2 \cdot 10^{-2}$ moles) | 10.14 g ($9.0 \cdot 10^{-2}$ moles) | 9.61 g ($8.5 \cdot 10^{-2}$ moles) | 9.94 g ($8.8 \cdot 10^{-2}$ moles) | 7.34 g ($6.5 \cdot 10^{-2}$ moles) |
| $C_6H_5SiCl_3$ | 9.223 g ($4.36 \cdot 10^{-2}$ moles) | 7.044 g ($3.33 \cdot 10^{-2}$ moles) | 6.008 g ($2.84 \cdot 10^{-2}$ moles) | 5.267 g ($2.49 \cdot 10^{-2}$ moles) | 3.977 g ($1.88 \cdot 10^{-2}$ moles) |
| Molar ratio $LiH/C_6H_5SiCl_3$ | 3.1 | 5.5 | 7.7 | 10.7 | 10.5 |
| Composition of medium after pouring $C_6H_5SiCl_3$ | | | | | |
| $C_6H_5SiH_3$ | 10.9% | 12.4% | 21.3% | 26.7% | 0% |
| $C_6H_5SiH_2Cl$ | 0% | 0% | 0% | 0% | 0% |
| $C_6H_5SiHCl_2$ | 0% | 0% | 0% | 0% | 0% |
| $C_6H_5SiCl_3$ | 23.1% | 21.6% | 4.6% | 0.2% | 35.1% |
| $C_6H_5Cl$ | 66.0% | 66.0% | 74.1% | 73.1% | 64.9% |

TABLE-continued

| | No. of experiment | | | | |
|---|---|---|---|---|---|
| | 1 | 2 | 3 | 4 | 5 |
| Composition of the medium after heating | | | | | |
| $C_6H_5SiH_3$ | 9.1% | 11.6% | 23.3% | 26.8% | 0% |
| $C_6H_5SiH_2Cl$ | 0.7% | 0.06% | 0% | 0% | 0% |
| $C_6H_5SiHCl_2$ | 7.3% | 4.0% | 0% | 0% | 0% |
| $C_6H_5SiCl_3$ | 17.0% | 18.3% | 1.4% | 0.2% | 35.1% |
| $C_6H_5Cl$ | 65.9% | 66.0% | 75.3% | 73.0% | 64.9% |
| After pouring $C_6H_5SiCl_3$ | | | | | |
| T.T. $C_6H_5SiCl_3$ | 48% | 53% | 90% | 99.6% | 0% |
| Selectivity $C_6H_5SiH_3$ | 100% | 100% | 100% | 100% | — |
| After heating | | | | | |
| T.T. $C_6H_5SiCl_3$ | 62% | 60% | 97% | 99.7% | 0% |
| Selectivity $C_6H_5SiH_3$ | 65% | 82% | 100% | 100% | — |

It will be seen from these experiments that a minimum $LiH/CH_6H_5SiCl_3$ molar ratio of approximately 8/1 is necessary for a degree of conversion of $C_6H_5SiCl_3$ of 100%.

In the case of lower ratios, unconverted $C_6H_5SiCl_3$ remains in the medium, which may react with $C_6H_5SiH_3$ during the subsequent heating to yield $C_6H_5SiHCl_2$ and $C_6H_5SiH_2Cl$ by redistribution reactions, catalyzed by TDA-1 and LiCl formed during the reaction:

$2C_6H_5SiCl_3 + C_6H_5SiH_3 \rightarrow 3C_6H_5SiHCl_2$

$C_6H_5SiCl_3 + 2C_6H_5SiH_3 \rightarrow 3C_6H_5SiH_2Cl$

The control experiment, No. 5, carried out without TDA-1, demonstrated the effectiveness of this catalyst.

EXAMPLE 3

Synthesis of $C_6H_5SiH_3$ by reduction of $C_6H_5SiCl_3$ with $CaH_2$

The apparatus was identical with that described in the preceding example.
Charges:
(i) 2.265 g TDA-1, or $0.70 \cdot 10^{-1}$ moles
(ii) 29.55 g $C_6H_5Cl$, or $26.26 \cdot 10^{-2}$ moles
(iii) 2.465 g $CaH_2$, or $5.56 \cdot 10^{-2}$ moles
4.74 g $C_6H_5SiCl_3$ ($2.24 \times 10^{-2}$ moles) were added over 15 min. No rise in temperature was observed.

The reaction medium was then heated to 95° C. over 4 hours.

The gas phase chromatographic analysis upon completion of the heating period evidenced the following composition (by weight):
$C_6H_5SiH_3$: 3.32%
$C_6H_5SiCl_3$: 7.76%
$C_6H_5Cl$: 88.92%
which corresponded to a degree of conversion of $C_6H_5SiCl_3$ of 46% and a selectivity in respect of $C_6H_5SiH_3$ of 100%.

EXAMPLE 4

Synthesis of $C_6H_5SiH_3$ by reduction of $C_6H_5SiCl_3$ with NaH

Into the apparatus used in the two preceding examples, the following materials were introduced:
(i) 3.037 g TDA-1, or $0.94 \times 10^{-2}$ mole,
(ii) 16.481 g $C_6H_5Cl$, or $14.64 \times 10^{-2}$ moles,
(iii) 4.812 g NaH, or $20.05 \times 10^{-2}$ moles.

Addition by pouring of $C_6H_5SiCl_3$ ($3.80 \times 10^{-2}$ moles) was over 30 min. The temperature of the reaction medium increased to 50° C.

Following the completion of the pouring, the reactor was heated for 0.5 hour to 120° C.

The composition of the reaction medium upon completion of the heating was the following (by weight):
$C_6H_5SiH_3$: 7.70%
$C_6H_5SiCl_3$: 20.14%
$C_6H_5Cl$: 72.16%
which corresponded to a degree of conversion of $C_6H_5SiCl_3$ of 43% and a selectivity in respect of $C_6H_5SiH_3$ of 100%.

EXAMPLE 5

Synthesis of $(CH_3)_2SiH_2$ by reduction of $(CH_3)_2SiCl_2$ with LiH

The same apparatus was used as in the experiments described in the preceding examples.

In order to prevent the elimination of the highly volatile $(CH_3)_2SiH_2$ (boiling point, $-20°$ C.) from the reaction medium, the reflux condenser surmounting the reactor was cooled by means of a cryogenic fluid at $-40°$ C., in place of water.
Charges:
(i) TDA-1: 1.905 g, or $0.59 \times 10^{-2}$ mole,
(ii) $C_6H_5Cl$: 8.184 g, or $7.27 \times 10^{-2}$ moles,
(iii) LiH: 0.923 g, or $11.61 \times 10^{-2}$ moles.

Addition of 3.27 g $(CH_3)_2SiCl_2$ ($2.53 \times 10^{-2}$ moles) was over 20 min.

The temperature of the reaction medium increased to 40° C.

The composition of the reaction medium, following the addition of $(CH_3)_2SiCl_2$ and standing for 1 hour at room temperature, was the following (by weight):
$(CH_3)_2SiH_2$: 15.36%

(CH₃)₂HSiCl: 0.51%
C₆H₅Cl: 84.13%
which corresponded to a degree of conversion of (CH₃)₂SiCl₂ of 100% and a selectivity in respect of (CH₃)₂SiH₂ of 98%.

EXAMPLE 6

Synthesis of SiH₄ by reduction of HSiCl₃ with LiH

The apparatus used in this example was as follows:
One liter Pyrex reactor equipped with a double jacket coil cooling system in which a cryogenic fluid was circulated at 0° C. and a magnetic agitator. The reactor was surmounted by a reflux condenser cooled to −20° C.

The TDA-1 and lithium hydride were charged after the flushing of the apparatus with argon (the experiment was carried out in the absence of a solvent).

HSiCl₃ was introduced at a constant rate by means of a volumetric pump. The reduction reaction, which took place at 0° C., was strongly exothermic.

The gaseous phase was analyzed in line by gas phase chromatography after measuring its flow rate and dilution by a flow of argon.

Charges:
(i) TDA-1: 485 g, or 1.5 moles
(ii) LiH: 47.7 g, or 6 moles.

HSiCl₃ was introduced at a rate of 79 ml/hr, or 0.78 mole/hr.

The temperature of the reaction medium rapidly increased to 45° C., in spite of vigorous cooling.

The composition of the gaseous phase exiting the reactor was the following:
H₂: 4.2%
SiH₄: 87.0%
H₃SiCl: 2.8%
H₂SiCl₂: 0.5%
HSiCl₃: 5.0%
SiCl₄: 0.5%
and the flow rate of the silane produced well corresponded to the rate of introduction of the HSiCl₃.

The reaction ceased when the degree of conversion of the LiH reached approximately 60%.

EXAMPLE 7

Synthesis of SiH₄ by reduction of HSiCl₃ with LiH

In this example, the reduction of HSiCl₃ was carried out in the presence of a solvent (C₆H₅Cl) and with a lower proportion of TDA-1.

The reactor with a magnetic agitator of the preceding example was replaced by a reactor equipped with a more efficient blade agitator system and was cooled by the circulation of a cryogenic fluid in a double jacket, while the remainder of the apparatus was identical to that described in said preceding example.

Charges:
(i) C₆H₅Cl: 1,238 g, or 11 moles
(ii) TDA-1: 48.5 g, or 0.15 mole
(iii) LiH: 143.1 g, or 18 moles.

Rates of the introduction of HSiCl₃: 95 ml/hr (0.94 mole/hr), then 192.4 ml/hr (1.89 mole/hr).

The small amount of TDA-1 in the medium made it necessary to limit the cooling to approximately 15° C. at the onset of the reaction in order to initiate same, as it would not commence at 0° C. Once the reaction began, the cryogenic fluid was again cooled to 0° C. to limit the temperature in the reactor.

The compositions of the gaseous phase exiting the reactor were the following (gas phase chromatographic analysis):

(a) For a flow rate of HSiCl₃ of 0.94 mole/hr:
H₂: 0.4%
SiH₄: 99.6%

The flow rate of the SiH₄ produced was exactly 0.94 mole/hr.

(b) For a HSiCl₃ flow rate of 1.89 mole/hr:
H₂: 0.3%
SiH₄: 99.0%
HSiCl₃: 0.7%

The flow rate of the SiH₄ produced was 1.86 mole/hr.

The reaction ceased when the degree of the conversion of LiH reached 84%.

While this invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A process for the preparation of a hydrogenosilane, comprising reducing a halogenosilane with an alkali or alkaline earth metal hydride in the presence of a catalytically effective amount of a sequestering agent having the general formula:

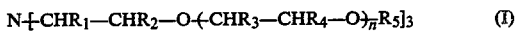

$$N\text{-}[CHR_1\text{---}CHR_2\text{---}O\text{-}(CHR_3\text{---}CHR_4\text{---}O)_n R_5]_3 \qquad (I)$$

wherein n ranges from 0 to 10, R₁, R₂, R₃ and R₄, which may be identical or different, are each hydrogen or an alkyl radical having from 1 to 4 carbon atoms, and R₅ is an alkyl or cycloalkyl radical having from 1 to 12 carbon atoms, a phenyl radical or a —C_mH_{2m}—φ or C_mH_{2m+1}—φ— radical, wherein m ranges from 1 to 12 and φ is phenyl.

2. The process as defined by claim 1, wherein said reduction is carried out in a solvent reaction medium.

3. The process as defined by claims 1 or 2, said halogenosilane having the formula R_nH_mSiX_{4−(n+m)}, wherein n is 0, 1, 2 or 3, m is 1, 2 or 3, R, if present, is an alkyl, aryl or alkoxy radical, and X is halogen.

4. The process as defined by claim 3, said sequestering agent (I) comprising:
tris-(3-oxabutyl)-amine of the formula: N—(CH₂—CH₂—O—CH₃)₃;
tris-(3,6-dioxaheptyl)-amine of the formula: N—(CH₂—CH₂—O—CH₂—CH₂—O—CH₃)₃;
tris-(3,6,9-trioxadecyl)-amine of the formula: N—(CH₂—CH₂—O—CH₂—CH₂—O—CH₂—CH₂—O—CH₃)₃;
tris-(3,6-dioxaoctyl)-amine of the formula: N—(CH₂—CH₂—O—CH₂—CH₂—O—C₂H₅)₃;
tris-(3,6,9-trioxaundecyl)-amine of the formula: N—(CH₂—CH₂—O—CH₂—CH₂—O—CH₂—CH₂—O—C₂H₅)₃;
tris-(3,6-dioxanonyl)-amine of the formula: N—(CH₂—CH₂—O—CH₂—CH₂—O—C₃H₇)₃;
tris-(3,6,9-trioxadodecyl)-amine of the formula: N—(CH₂—Ch₂—O—CH₂—CH₂—O—CH₂—CH₂—O—C₃H₇)₃;
tris-(3,6-dioxadecyl)-amine of the formula: N—(CH₂—CH₂—O—CH₂—CH₂—O—C₄H₉)₃;

tris-(3,6,9-trioxatridecyl)-amine of the formula: N—(CH₂—CH₂—O—CH₂—CH₂—O—CH₂—CH₂—O—C₄H₉)₃;

tris-(3,6,9,12-tetraoxatridecyl)-amine of the formula: N—(CH₂—CH₂—O—(CH₂—CH₂—O)₃—CH₃)₃;

tris-(3,6,9,12,15,18-hexaoxanonadecyl)-amine of the formula: N—(CH₂—CH₂—O—(CH₂—CH₂—O)₅—CH₃)₃;

tris-(3,6-dioxa-4-methylheptyl)-amine of the formula:

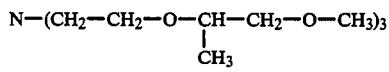

tris-(3,6-dioxa-2,4-dimethylheptyl)-amine of the formula:

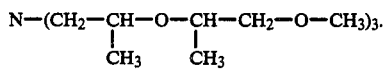

5. The process as defined by claim 3, wherein said sequestering agent (I), R₁, R₂, R₃ and R₄ are each hydrogen or methyl.

6. The process as defined by claim 5, wherein said sequestering agent (I), n ranges from 0 to 6, and R₅ is an alkyl radical having from 1 to 4 carbon atoms.

7. The process as defined by claim 3, wherein said alkali or alkaline earth metal hydride comprises lithium hydride, sodium hydride, calcium hydride or magnesium hydride.

8. The process as defined by claim 3, wherein said halogenosilane comprises silicon tetrachloride, trichlorosilane, dichlorosilane, dimethyldichlorosilane, methylhydrogenodichlorosilane, diphenyldichlorosilane, phenyltrichlorosilane, methylphenyldichlorosilane, phenyltrichlorosilane, methylphenyldichlorosilane or diethyldichlorosilane, or mixtures thereof.

9. The process as defined by claim 3, wherein said sequestering agent catalyst comprises a cross-linked organic polymeric substrate having a plurality of functional groups grafted thereon, said functional groups having the general formula:

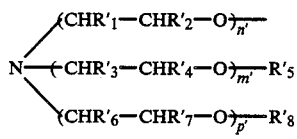

wherein R'₁, R'₂, R'₃, R'₄, R'₆ and R'₇, which may be identical or different, are each a hydrogen atom or an alkyl radical having from 1 to 4 carbon atoms, R'₅ and R'₈, which also may be identical or different, are each a hydrogen atom, an alkyl or cycloalkyl radical having from 1 to 12 carbon atoms, a phenyl radical, a —C_qH_{2q'}—φ or C_{q'}H_{2q'+1}—φ— radical, with q' being greater than or equal to 1 and less than or equal to 12, and wherein n', m' and p', which also may be identical or different, are greater than or equal to 1 and less than or equal to 10.

10. The process as defined by claim 9, wherein said functional groups (II), R'₁, R'₂, R'₃, R'₄, R'₆ and R'₇, which may be identical or different, are each a hydrogen atom or a methyl radical and R'₅ and R'₈, which may be identical or different, are each a hydrogen atom or an alkyl radical having from 1 to 4 carbon atoms.

11. The process as defined by claim 10, wherein said functional groups (II), n', m' and p', which may be identical or different, each range from 1 to 6.

12. The process as defined by claim 9, said functional groups (II) having at least one of the formulae:

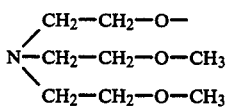

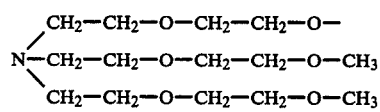

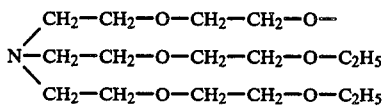

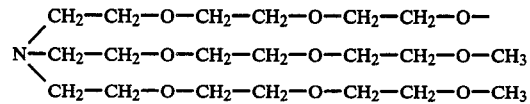

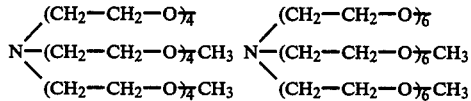

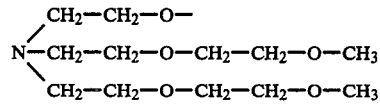

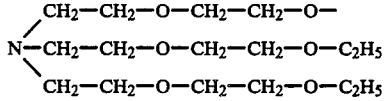

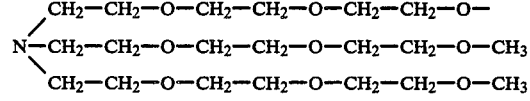

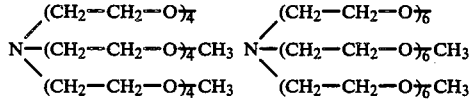

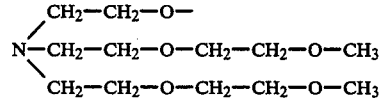

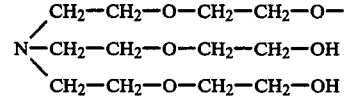

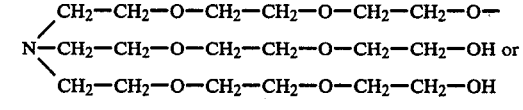

-continued

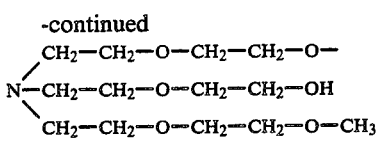

13. The process as defined by claim 3, wherein the molar ratio between said sequestering agent (I) and said alkali or alkaline earth metal hydride ranges from 5 to 0.0001.

14. The process as defined by claim 13, said molar ratio ranging from 0.5 to 0.001.

15. The process as defined by claim 13, wherein said halogenosilane is reduced with a stoichiometric excess of from 10 to 300 molar % of said hydride.

* * * * *